US011357883B1

(12) United States Patent
Kim et al.

(10) Patent No.: US 11,357,883 B1
(45) Date of Patent: Jun. 14, 2022

(54) METHOD FOR PREPARING ABSORBABLE HAEMOSTATIC COMPOSITION FOR BODY AND HAEMOSTATIC COMPOSITION PREPARED THEREBY

(71) Applicant: MANTIZ LOGITECH CO., LTD., Daegu (KR)

(72) Inventors: Eui Jun Kim, Daegu (KR); Il Hwan Lee, Busan (KR); Hae Jun Jeong, Daegu (KR); Seong Hwan Kim, Daegu (KR)

(73) Assignee: MANTIZ LOGITECH CO., LTD., Daegu (KR)

( * ) Notice: Subject to any disclaimer, the term of this patent is extended or adjusted under 35 U.S.C. 154(b) by 0 days.

(21) Appl. No.: 17/542,946

(22) Filed: Dec. 6, 2021

(30) Foreign Application Priority Data

Dec. 8, 2020 (KR) .......................... 10-2020-0170826

(51) Int. Cl.
*A61L 15/32* (2006.01)
*A61L 15/18* (2006.01)
*A61L 15/42* (2006.01)
*A61L 26/00* (2006.01)

(52) U.S. Cl.
CPC ............. *A61L 15/18* (2013.01); *A61L 15/325* (2013.01); *A61L 15/425* (2013.01); *A61L 26/0004* (2013.01); *A61L 26/0038* (2013.01); *A61L 2400/04* (2013.01)

(58) Field of Classification Search
None
See application file for complete search history.

(56) References Cited

FOREIGN PATENT DOCUMENTS

| KR | 10-2001-0074825 A | 8/2001 |
| KR | 10-2015-0027134 A | 3/2015 |
| KR | 10-1791893 B1 | 11/2017 |
| KR | 10-2017-0143369 A | 12/2017 |

OTHER PUBLICATIONS

"Notice of Final Rejection" Office Action issued in KR 10-2020-0170826; mailed by the Korean Intellectual Property Office dated May 11, 2021.
"Grant of Patent" Office Action issued in KR 10-2020-0170826; mailed by the Korean Intellectual Property Office dated May 27, 2021.

*Primary Examiner* — Kevin S Orwig
(74) *Attorney, Agent, or Firm* — Studebaker & Brackett PC

(57) ABSTRACT

The present disclosure relates to a method for preparing an absorbable haemostatic composition for the body and the haemostatic composition prepared thereby, and the present disclosure is for providing a method for preparing an absorbable haemostatic composition for the body and the haemostatic composition prepared thereby, wherein the haemostatic composition can be used directly on the wound site when bleeding occurs in the surgical area such as surgical operation, trauma, etc. so that hemostasis can be effectively performed, the haemostatic composition can perform wound sealing, tissue repairing promotion, wound surface tissue protection, infection prevention, etc., the haemostatic composition is contained in haemostatic products such as gauze (cotton yarn), sponge, etc. to accelerate the hemostasis speed of the bleeding site and enable rapid hemostasis to be able to shorten the hemostasis time at the same time.

1 Claim, 5 Drawing Sheets

Example 1  Example 2  Example 3  Example 4  Example 5

Before induction of bleeding
(Left) In-house developed
    product
(Right) Competitor product A Hemostasis completed
after 2 minutes
(Left) In-house developed
    product (O)
(Right) Competitor product A (O)

Rebleeding after 5 minutes
(Left) In-house developed
    product (×)
(Right) Competitor product A (O)

METHOD FOR PREPARING ABSORBABLE HAEMOSTATIC COMPOSITION FOR BODY AND HAEMOSTATIC COMPOSITION PREPARED THEREBY

CROSS-REFERENCE TO RELATED APPLICATIONS

This application claims the priority of Korean Patent Application No. 10-2020-0170826 filed on Dec. 8, 2020, in the Korean Intellectual Property Office, the disclosure of which is incorporated herein by reference.

BACKGROUND

Field

The present disclosure relates to a method for preparing an absorbable haemostatic composition for the body and the haemostatic composition prepared thereby, and more particularly, to a method for preparing an absorbable haemostatic composition for the body, the composition which is contained in gauze, sponge, etc. used as haemostatic products in the surgical area to promote hemostasis and enable rapid hemostasis at the same time, and which contains gelatin and kaolin to effectively act on a bleeding site, thereby having excellent hemostasis action and haemostatic effect, and the haemostatic composition prepared thereby.

Description of the Related Art

Blood is composed of plasma, which is a liquid component, accounting for 55% of the total blood, and blood cells, a cellular component, accounting for the remaining 45%. The blood cells include red and white blood cells, other blood cells, and platelets dispersed in a liquid phase.

In general, hemostasis is carried out at the bleeding site during bleeding in the surgical area, and a haemostatic method includes methods of hemostasis using a ligation method, a compression method, an electrocoagulation method, a physiologically active material such as thrombin, fibrin glue, or the like, etc.

Here, in the case of arterial bleeding with a clear bleeding point, the ligation method or the electrocoagulation method is used, and in the case of venous bleeding, sufficient hemostasis is possible only by the ligation method or compression.

However, when capillary bleeding from parenchymal organs or bleeding from vascular anastomosis occurs, there are cases where the above-described haemostatic methods are not effective. Due to this, in the field of cardiovascular surgery, it may cause difficulties in hemostasis when surgery is performed using the anticoagulant heparin, when there is a tendency to bleed due to liver failure, or when performing a surgery accompanied by extensive dissection operation even during general surgery.

As described above, when difficulties are caused in hemostasis, there is a demand for a haemostatic method and a haemostatic product which accelerate the blood clotting reaction just by contacting the bleeding surface, and which are capable of performing hemostasis so that a locally absorbable haemostatic agent, which prevents bleeding by rapidly forming a thrombus, not only shortens the operation time, but also prevents even post-surgery rebleeding.

Meanwhile, as a general locally absorbable haemostatic agent, a haemostatic agent made of cellulose, a haemostatic agent made of gelatin, a haemostatic agent made of aterocollagen, and a haemostatic agent made of microfibrous collagen are common.

Here, the haemostatic agent made of cellulose has had advantages of being inexpensive and excellent in operability, but there has been a problem in that the haemostatic ability is not sufficient since the material itself does not have a physiologically active action, the haemostatic agent made of gelatin, when it contains blood, has had problems in that the surface is gelled and the adhesiveness of the bleeding wound is damaged so that it is easy to peel, the haemostatic agent made of aterocollagen has had a toxicity problem with respect to chemicals since a crosslinking agent is used to fiberize atherocollagen, and the haemostatic agent made of microfibrous collagen has had problems in that the haemostatic effect is not large since it is formed to allow the microfibers of collagen to flow and disperse into the bleeding wound site, and static electricity is generated so that it is attached to the hand or tweezers when used.

Therefore, there is a demand for a haemostatic agent which has high haemostatic ability, is non-toxic to the living body when used in bleeding sites, is similar to living tissue, has no antigenicity that invades the living body to form antibodies, is easily decomposed and absorbed in the living body, and has an inexpensive manufacturing cost.

PRIOR ART DOCUMENT

Patent Document (Patent Document 1) Korean Patent Publication No. 10-2001-0074825

SUMMARY

The present disclosure is intended to solve the above problems, and an object of the present disclosure is to provide a method for preparing an absorbable haemostatic composition for the body and the haemostatic composition prepared thereby, wherein the haemostatic composition can be used directly on the wound site when bleeding occurs in the surgical area such as surgical operation, trauma, etc. so that hemostasis can be effectively performed, the haemostatic composition can perform wound sealing, tissue repairing promotion, wound surface tissue protection, infection prevention, etc., the haemostatic composition is contained in haemostatic products such as gauze (cotton yarn), sponge, etc. to accelerate the hemostasis speed of the bleeding site and enable rapid hemostasis to be able to shorten the hemostasis time at the same time, and the haemostatic composition can prevent a situation of putting the patient at risk due to excessive bleeding.

Further, an object of the present disclosure is to provide a method for preparing an absorbable haemostatic composition for the body and a haemostatic composition prepared thereby, wherein the haemostatic composition has excellent haemostasis action and haemostatic effect by containing gelatin and kaolin and effectively acting on the bleeding site, has biocompatibility, is easily absorbed and decomposed in vivo, can respond quickly to capillary bleeding or bleeding from vascular anastomosis, can be effectively adapted to hemostasis, can promote the formation of platelet plugs by activating platelet adhesion, and acts more efficiently on the bleeding site to be able to achieve a continuous hemostasis effect.

Further, technical tasks to be achieved by the present disclosure are not limited to the technical tasks mentioned above, and other technical tasks not mentioned can be clearly understood by those of ordinary skill in the art to which the present disclosure pertains from the description below.

In order to achieve the above objects, a method for preparing an absorbable haemostatic composition for the body according to the present disclosure comprises the steps of: mixing at least any one of gelatin, collagen, collagen peptide, chitosan, polymer haemostatic material, and beeswax with sterile distilled water; solizing the mixture; mixing kaolin with the solized mixture; and imparting viscosity to the mixed solution with which kaolin has been mixed.

Here, when mixing at least one of gelatin, collagen, collagen peptide, chitosan, polymer haemostatic material, and beeswax with sterile distilled water, the at least one thereof is mixed in an amount of 1 to 10 parts by weight with respect to 100 parts by weight of sterile distilled water.

Preferably, when solizing the mixture in which the at least one of gelatin, collagen, collagen peptide, chitosan, polymer haemostatic material, and beeswax has been mixed with sterile distilled water, the solization is performed by stirring the mixture to 100 to 500 rpm in a temperature range of 40 to 100° C. for 1 to 2 hours.

Here, when mixing kaolin with the solized mixture, kaolin is mixed in an amount of 1 to 10 parts by weight with respect to 100 parts by weight of sterile distilled water.

Preferably, when mixing kaolin with the solized mixture, kaolin and the solized mixture are stirred and mixed to 100 to 500 rpm in a temperature range of 40 to 100° C. for 20 minutes to 1 hour.

At this time, when imparting viscosity to a mixed solution with which kaolin has been mixed, the mixed solution is put into a cooler, and a cooling plate provided on the bottom surface of the cooler is stirred to 100 to 500 rpm in a temperature range of 0 to 10° C., thereby imparting a viscosity of 3,000 cps to the mixed solution.

Meanwhile, the haemostatic composition is prepared by mixing 1 to 10 parts by weight of at least any one of gelatin, collagen, collagen peptide, chitosan, polymer haemostatic material, and beeswax with 100 parts by weight of sterile distilled water, stirring the sterile distilled water-mixed mixture to 100 to 500 rpm at a temperature of 40 to 100° C. for 1 to 2 hours to solize the mixture, mixing 1 to 10 parts by weight of kaolin with the solized mixture to stir kaolin and the solized mixture to 100 to 500 rpm in a temperature range of 40 to 100° C. for 20 minutes to 1 hour, injecting the mixed solution with which kaolin has been mixed into a cooler, stirring a cooling plate of the cooler to 100 to 500 rpm in a temperature range of 0 to 10° C. to impart a viscosity of 3,000 to the mixture.

As described above, the absorbable haemostatic composition for the body according to the present disclosure having the above-mentioned configuration can achieve effects that it can be used directly on a wound site when there is bleeding due to causes such as surgical operation, trauma, etc., can be used directly on the wound site to enable effective hemostasis, can perform wound sealing, tissue repairing promotion, wound surface tissue protection, infection prevention, etc., can be used in a state that it is contained in haemostatic products such as gauze (cotton yarn), sponge, etc. so that it accelerates the hemostasis speed of the bleeding site and enables rapid hemostasis to enable the hemostasis time to be shortened at the same time, and can prevent a situation of putting the patient at risk due to excessive bleeding.

Further, the absorbable haemostatic composition for the body according to the present disclosure has excellent haemostasis action and haemostatic effect by containing gelatin and kaolin and effectively acting on a bleeding site, has biocompatibility, is easily absorbed and decomposed in vivo, can respond quickly to capillary bleeding or bleeding from vascular anastomosis, has excellent hemostasis action by preventing rebleeding, enables effective hemostasis to be achieved for the affected area due to this, has high hemostasis ability, is non-toxic to the living body when used on the bleeding site, is similar to a living tissue, has no antigenicity invading the living body to form antibodies, has a low manufacturing cost, and acts more efficiently on the bleeding site to achieve a continuous haemostatic effect.

DETAILED DESCRIPTION

Figure 1:
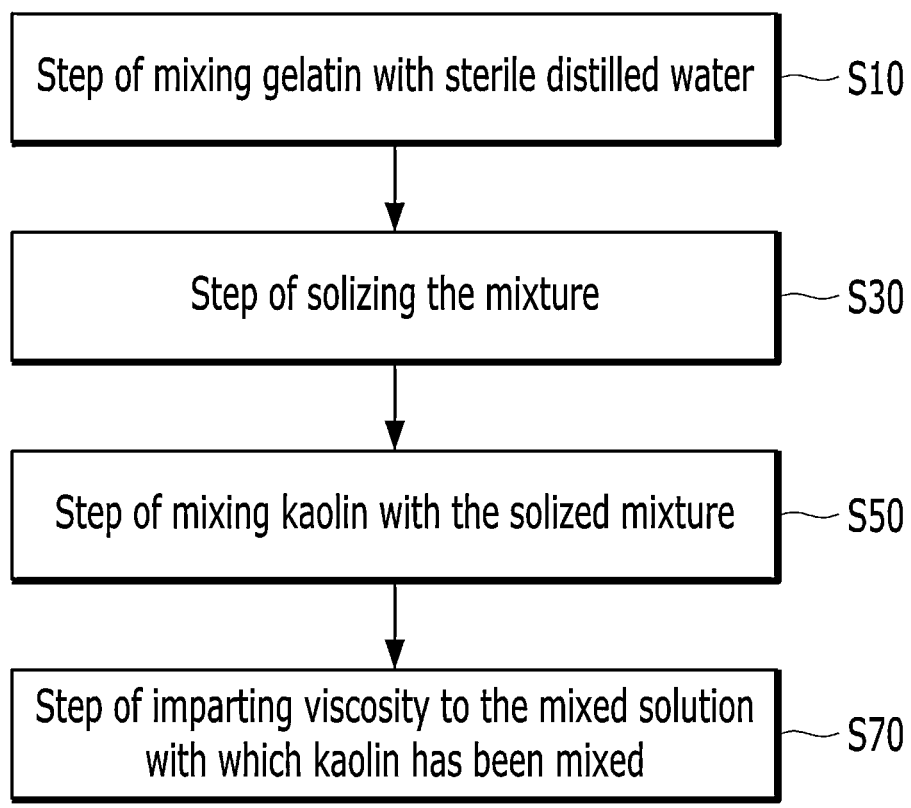
FIG. 1 is a flowchart schematically showing a method for preparing an absorbable haemostatic composition for the body according to the present disclosure.

Advantages and characteristics of the present disclosure and a method of achieving the advantages and characteristics will be clear by referring to exemplary embodiments described later in detail together with the accompanying drawings.

However, the present disclosure is not limited to exemplary embodiment disclosed below, but will be implemented in various different forms.

In the present specification, the present embodiment is provided to complete the disclosure of the present disclosure, and to fully inform those of ordinary skill in the art to which the present disclosure pertains of the scope of the present disclosure.

Further, the present disclosure is only defined by the scope of the claims.

Therefore, in some embodiments, well-known elements, well-known operations, and well-known techniques have not been specifically described in order to avoid being obscurely construed of the present disclosure.

Further, like reference numerals refer to like elements throughout the specification, and terms used (referred to) in the present specification are for the purpose of describing the exemplary embodiments and are not intended to limit the present disclosure.

In the present specification, the singular form also includes the plural form unless specifically stated in the phrase, and elements and operations referred to as 'comprising (or having)' do not exclude the presence or addition of one or more other elements and operations.

Unless otherwise defined, all terms (including technical and scientific terms) used in the present specification may be used with the meaning commonly understood by those of ordinary skill in the art to which the present disclosure pertains.

Further, terms defined in a commonly used dictionary are not to be interpreted ideally or excessively unless they are defined.

Figure 2:
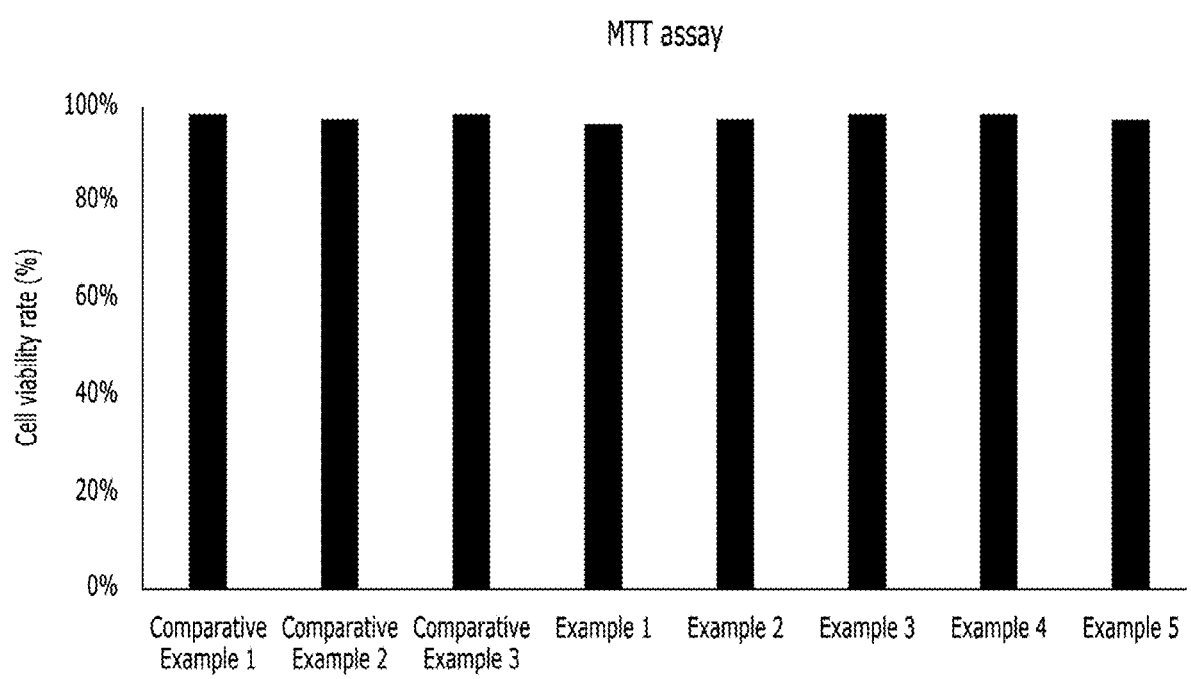
FIG. 2 is a view showing the cytotoxicity test results according to Examples and Comparative Examples of the haemostatic composition prepared according to the method for preparing the absorbable haemostatic composition for the body according to the present disclosure.
Figure 3:
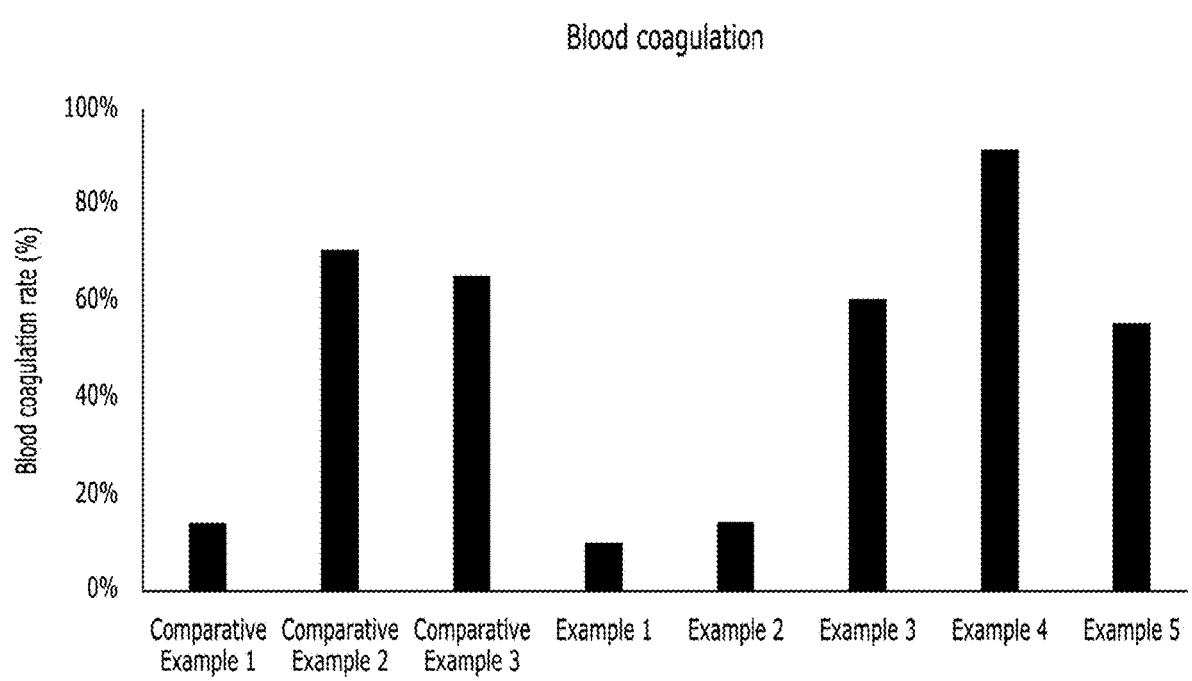
FIG. 3 is a view showing blood clotting test results according to Examples and Comparative Examples of the haemostatic composition prepared according to the method for preparing the absorbable haemostatic composition for the body according to the present disclosure.
Figure 4:
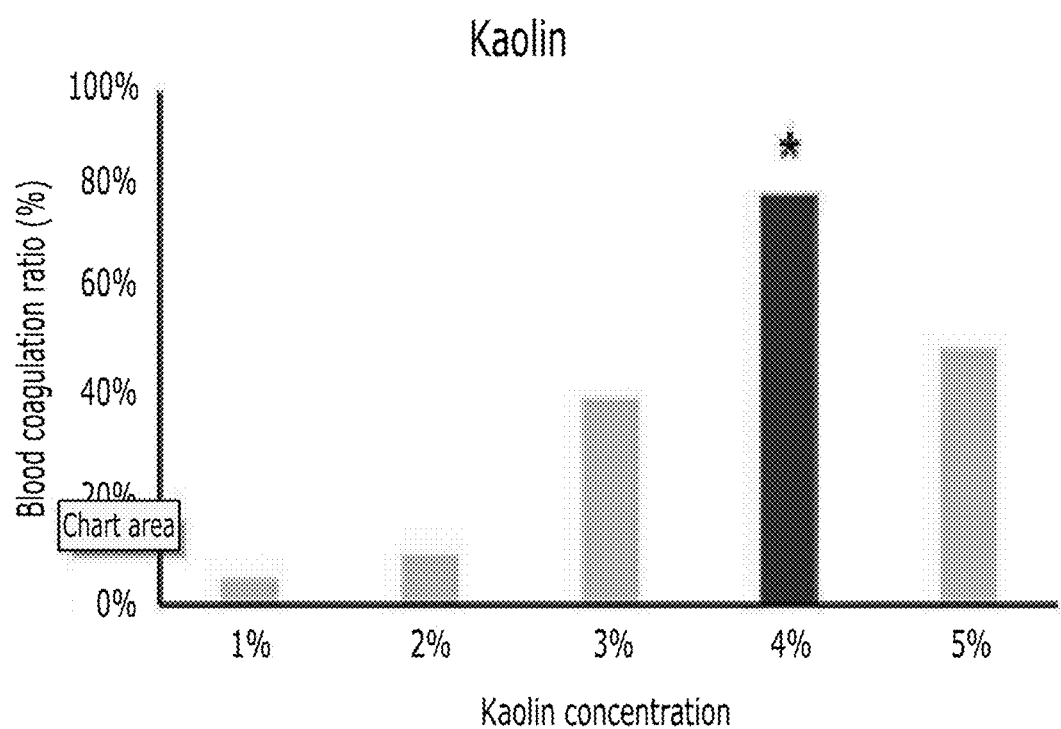
FIG. 4 is a view showing the blood clotting rates depending on the contents of kaolin mixed in the haemostatic composition prepared according to the method for preparing the absorbable haemostatic composition for the body according to the present disclosure.
Figure 5:
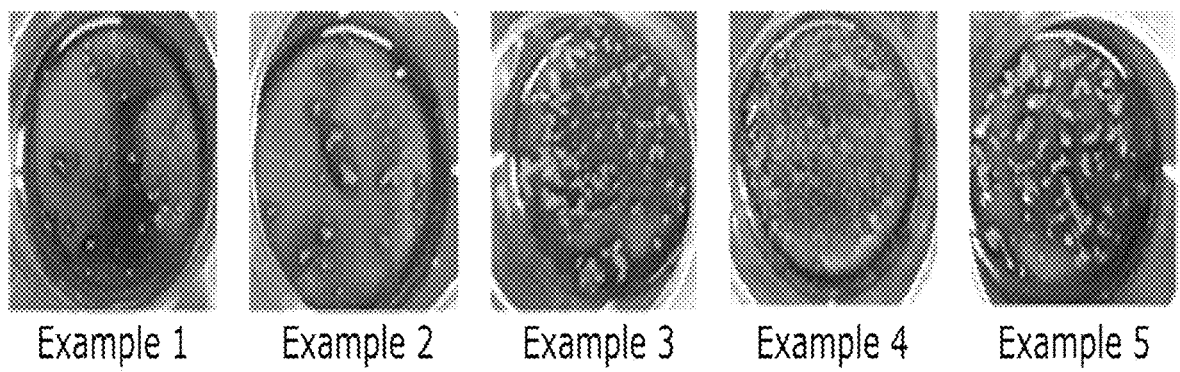
FIG. 5 is a view showing an appearance in which blood is coagulated according to Examples of the haemostatic composition prepared according to the method for preparing the absorbable haemostatic composition for the body according to the present disclosure.
Figure 6:
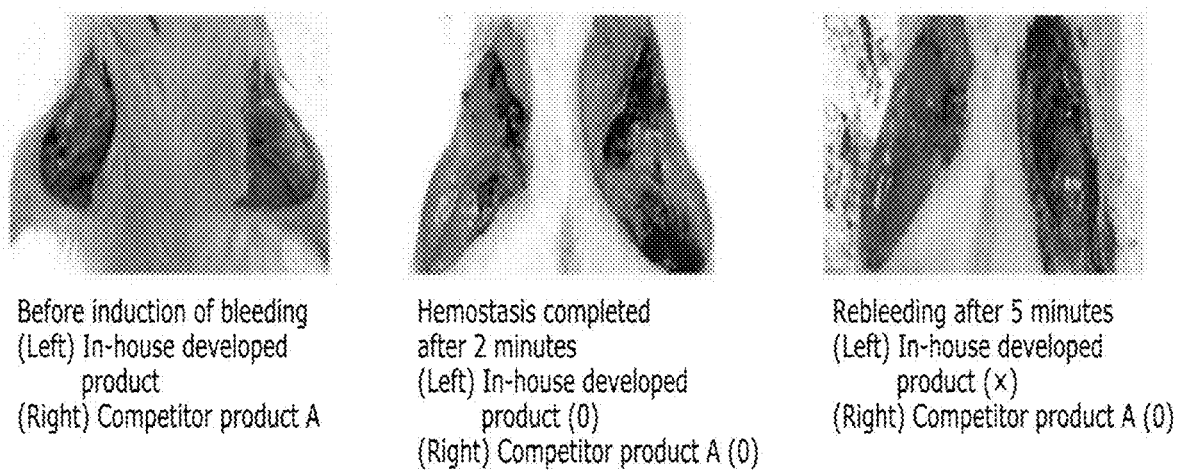
FIG. 6 is a view showing the rebleeding test results after hemostasis of the haemostatic composition prepared according to the method for preparing the absorbable haemostatic composition for the body according to the present disclosure.

Hereinafter, preferred embodiments of the present disclosure will be described with reference to the accompanying drawings. FIG. 1 is a flowchart schematically showing a method for preparing an absorbable haemostatic composition for the body according to the present disclosure, FIG. 2 is a view showing the cytotoxicity test results according to Examples and Comparative Examples of the haemostatic composition prepared according to the method for preparing the absorbable haemostatic composition for the body according to the present disclosure, FIG. 3 is a view showing blood clotting test results according to Examples and Comparative Examples of the haemostatic composition prepared according to the method for preparing the absorbable haemostatic composition for the body according to the present disclosure, FIG. 4 is a view showing the blood clotting rates depending on the contents of kaolin mixed in the haemostatic composition prepared according to the method for preparing the absorbable haemostatic composition for the body according to the present disclosure, FIG. 5 is a view showing an appearance in which blood is coagulated according to Examples of the haemostatic composition prepared according to the method for preparing the absorbable haemostatic composition for the body according to the present disclosure, and FIG. 6 is a view showing the rebleeding test results after hemostasis of the haemostatic composition prepared according to the method for preparing the absorbable haemostatic composition for the body according to the present disclosure.

As shown in the drawings, the method for preparing the absorbable haemostatic composition for the body according to the present disclosure is as follows.

First, a gelatin is injected into and mixed with sterile distilled water in a mixing tank (S10).

The gelatin is a kind of derived proteins obtained from collagen which is a natural protein constituting animal hides, tendons, cartilage, etc. It has a transparent color, and allows multiple absorption pores in the surface of gelatin to promote the division of platelets through the activation of enzymes that induce natural clotting, helping rapid hemostasis action.

When such a gelatin is impregnated with a liquid, it absorbs moisture and swells. When impregnated with a liquid and heated, it melts and becomes a colloidal sol state to increase the viscosity, and when cooled, it hardens to form a gel state.

Here, the gelatin in the gel state is changed to the sol state again at high temperatures, and when the gelatin in the sol state is cooled again, the flexibility to the gel state and the sol state is determined depending on the effect of temperature, such as changing to the gel state.

In an embodiment of the present disclosure, although the gelatin is injected into and mixed with sterile distilled water, it is also possible that at least one of gelatin, collagen, collagen peptide, chitosan, polymer haemostatic material, or beeswax is contained in sterile distilled water.

Here, collagen is a major tissue-forming protein that fills the extracellular space of various connective tissues in the animal body, and depending on the degree of mineralization, it is hard as in bone, flexible as in tendon, or there may be a gradient from the hard part to the flexible part as seen in cartilage.

Collagen accounts for 1 to 2% of muscle tissue and about 6% in strong, tendon-rich muscles. Fibroblasts, the most common cells in the body, produce and secrete collagen. Gelatin, which is widely used in the food and pharmaceutical industries, is one obtained by irreversibly hydrolyzing collagen.

Further, collagen peptide is one obtained by enzymatically decomposing gelatin to reduce the molecular weight to about several thousands or several hundreds. That is, collagen has a property of being melted by heating, one obtained by denaturing collagen by heating is gelatin due to this, and it refers to one obtained by enzymatically decomposing gelatin again to make it into a small one with a microscopic size.

The size of the molecular weight of such collagen peptide is reduced to facilitate digestion and absorption so that it can be rapidly absorbed into the human body.

Meanwhile, chitosan is a substance obtained by deacetylating chitin contained in crustaceans, and is processed to be easily absorbed by the human body. Here, characteristics of chitosan inhibit aging, strengthen immunity, and prevent diseases by activating degenerated cells. Further, the characteristics of chitosan regulate the biorhythms along with the function of activating the living body's natural healing ability.

Efficacies of such chitosan are that it serves to absorb and excrete excess harmful cholesterol from the body, that is, does a decholesterol action, does an anticancer action of suppressing the proliferation of cancer cells, and adsorbs chloride ions causing a rise in blood pressure, suppresses absorption thereof in the intestines, and then discharges them out of the body to do a blood pressure increase-inhibiting action, proliferate effective bacteria in the intestine, and activate the cells.

In addition, it has effects such as blood sugar control, liver function improvement action, excretion of heavy metals and pollutants from the body, etc.

Further, the polymer haemostatic material is used as a material for a waterproof cloth that covers the soft skin to stop bleeding, a cell adhesive that connects the wound, a filler that fills open wounds, an absorbent dressing for moisture control, a dressing that does an antibacterial action, a thin transparent dressing that protects from bacteria and germs, a device for safely fixing and covering a catheter and the place where the catheter is inserted, etc.

Here, the polymer haemostatic material includes a fibrin adhesive or a cyano acrylate adhesive.

The fibrin adhesive is one using the principle that when chondrocytes in a liquid state are mixed with an adhesive (biological fibrin ingredients) and injected into the damaged area, the mixture is slowly hardened and adhered. It is made from the human body's own ingredients, and can utilize various reactions of natural hemostasis.

In the final stage of clotting, thrombin protein catalyzes the polymerization of fibrinogen to form insoluble fibrin.

In the process of natural clotting, such a fibrin adhesive allows these protein chains to confine red blood cells and form clumps that block blood from flowing. In fabrin adhesive products, substances with a concentration higher than that of human body's serum come out of storage bodies separated from each other and react to form a protein mass and attach strongly to cells to perform hemostasis or adhere the cells together.

Products commercialized with such an fabrin adhesive reinforce other catalysts and elements that prevent dissolution and reabsorption of proteins.

Meanwhile, a cyano acrylate adhesive is widely used for medical purposes since it provides a fast curing speed and strong adhesion, and it is in the spotlight as a material for suturing clean wounds formed on the skin so that it is used as a haemostatic agent in an emergency.

In an embodiment of the present disclosure, although a fabrin adhesive or a cyano acrylate adhesive has been applied as a polymer haemostatic material, an alginic acid salt or a hydrogel may be further included.

Here, alginates are natural polymers and can be obtained from brown seagrass, and they have R-(1,4) bonds as linear D-mannuronic acid and L-guluronic acid residues.

An alginate polymer, which is a sodium salt, has solubility, and when the sodium salt is pushed into calcium chloride, it can be pulled out into a fibrous tissue, and when a sodium salt solution and calcium chloride are mixed, it can be made into a gel.

Both fibrous tissue and gel absorb large amounts of water or wound exudate, and either make a gauze or a loose string with the fibrous tissue and place it on swallowing wounds to immobilize or absorb the exudate.

The gel has moderate adhesiveness so that it comes off cleanly from the wound and does not leave residues such as fibrous tissue so that it does not interfere with wound healing.

Meanwhile, the hydrogel can fill the wound with it by making materials such as a gel made from polysaccharide, which is a hydrophilic polymer, or poly(N-vinylpyrrolidone), like a pad or thread, and enables the wound to be healed or enables the growth of bacteria to be blocked by containing bioactive substances therein.

Further, the polymer haemostatic material may further include rayon, polyester, and calcium alginate fibers, and if hemostasis is easy, other various materials can be further included, but the present disclosure is not limited thereto.

Meanwhile, beeswax is a liquid oil that is a substance produced in the body by enzymatic action of sugars collected from flowers by bees. Its main ingredient is a polymer of high molecular hydrocarbons, palmitic acid esters of melicyl alcohol, and cerotic acid. It is an amorphous substance with adhesive properties and is also used as a raw material for cosmetics, insulating agents, floor paints, and candles.

At this time, when mixing at least one of gelatin, collagen, collagen peptide, chitosan, polymer haemostatic material, and beeswax with sterile distilled water, 1 to 10 parts by weight of the at least one thereof is mixed with respect to 100 parts by weight of sterile distilled water.

Preferably, when mixing at least one of gelatin, collagen, collagen peptide, chitosan, polymer haemostatic material, and beeswax with sterile distilled water, 5 to 8 parts by weight of the at least one thereof is mixed with respect to 100 parts by weight of sterile distilled water.

As described above, after mixing the at least one of gelatin, collagen, collagen peptide, chitosan, polymer haemostatic material, and beeswax with sterile distilled water, the mixture is solized (S30).

Here, when solizing the mixture, the mixture is stirred to 100 to 500 rpm in a temperature range of 40 to 100° C. for 1 to 2 hours to solize the mixture.

Preferably, the mixture is stirred to 300 rpm at a temperature of 70 to 80° C. for 1 hour to solize the mixture.

Kaolin is mixed with the mixture solized in this way (S50).

Kaolin is a naturally produced white or milky white hydrous aluminum silicate powder, and the chemical components include Al2Si2O5(OH)4 and pyrophyllite.

Such kaolin may contact Factor XII (Hageman Factor) among plasma proteins present in blood to promote blood clotting through interactions.

Further, kaolin plays a role of causing deformation by activating Factor XII, Factor XI (plasma thromboplastin precursor, Thromboplastin Antecedent), Prekallikrein, etc.

In particular, Factor XII is involved in the activation, and the sensitivity of kallikrein, a plasma component of Factor XII, is increased due to kaolin to significantly accelerate the activation rate, thereby promoting blood clotting and enabling the haemostatic effect of the wound to be improved.

Here, when mixing kaolin with the solized mixture, 1 to 10 parts by weight of kaolin is mixed with respect to 100 parts by weight of sterile distilled water.

Preferably, when mixing kaolin with the solized mixture, 3 to 6 parts by weight of kaolin is mixed with respect to 100 parts by weight of sterile distilled water.

Meanwhile, when mixing kaolin with the solized mixture, they are mixed by stirring them to 100 to 500 rpm in a temperature range of 40 to 100° C. for 20 minutes to 1 hour.

Preferably, when mixing kaolin with the solized mixture, they are mixed by stirring them to 350 to 450 rpm at a temperature of 60 to 80° C. for 30 minutes.

As described above, viscosity is imparted to the mixed solution in which kaolin is mixed (S70).

Here, when imparting viscosity to the mixed solution in which the kaolin has been mixed, after injecting the mixed solution into a cooler, the mixed solution is stirred to 100 to 500 rpm in a temperature range of 0 to 10° C. of a cooling plate rotatably provided on the bottom surface of the cooler, thereby imparting a viscosity of 3,000 cps.

In this way, the mixed solution that has reached the viscosity of 3,000 cps is again stirred to 100 to 200 rpm in a temperature range of 23 to 28° C. Preferably, the mixed solution that has reached the viscosity of 3,000 cps is stirred to 100 to 200 rpm at a temperature of 25° C.

EXAMPLES AND COMPARATIVE EXAMPLES

Hereinafter, the present disclosure will be specifically described with reference to Examples and Comparative Examples. An average person skilled in the art to which the present disclosure pertains can change the present disclosure in various other forms other than the compositions described in the Examples below, and the following Examples only illustrate the present disclosure, but should not be construed as an intention of limiting the scope of the technical spirit of the present disclosure to the scope of the following Examples.

Example 1

5% by weight of gelatin was added to a mixing tank based on the weight of sterile distilled water, and they were heated at a temperature of 80° C. for 1 hour and mixed. Then, whether the gelatin had been solized or not was checked, and 1% by weight of a kaolin solution was added to the solized mixed solution and mixed, followed by stirring to a constant speed of 450 rpm at a temperature of 80° C. for 30 minutes. After the stirred mixed solution was injected into a cooler and stirred to 150 rpm at a temperature of 4° C. to impart a viscosity of 3,000 cps to the mixed solution, and bubbles were removed from the mixed solution to which the viscosity of 3,000 cps had been imparted at room temperature of 25° C., the bubble-removed mixed solution was infused into a syringe.

Example 2

The process was performed in the same manner as in Example 1 except that 2% by weight of the kaolin solution was added and mixed.

Example 3

The process was performed in the same manner as in Example 1 except that 3% by weight of the kaolin solution was added and mixed.

Example 4

The process was performed in the same manner as in Example 1 except that 4% by weight of the kaolin solution was added and mixed.

Example 5

The process was performed in the same manner as in Example 1 except that 5% by weight of the kaolin solution was added and mixed.

Comparative Example 1

5% by weight of gelatin was added to a mixing tank based on the weight of sterile distilled water, and they were heated at a temperature of 80 for 1 hour to mix them. Then, after checking whether the gelatin had been solized or not, the solized mixed solution was injected into a cooler and stirred to 150 rpm at a temperature of 4° C. to impart a viscosity of 3,000 cps to the mixed solution, and bubbles were removed from the mixed solution to which the viscosity of 3,000 cps had been imparted at room temperature of 25° C., the bubble-removed mixed solution was infused into a syringe.

Comparative Example 2

After adding and mixing 3% by weight of a kaolin solution based on the weight of sterile distilled water in a mixing tank, stirring the mixture to a constant speed of 450 rpm for 30 minutes, injecting the stirred mixture into a cooler and stirring the mixture to 150 rpm at a temperature of 4° C. to impart a viscosity of 3,000 cps to a mixed solution, and removing bubbles from the mixed solution to which the viscosity of 3,000 cps had been imparted at room temperature of 25° C., the bubble-removed mixed solution was infused into a syringe.

Comparative Example 3

3% by weight of gelatin was added to a mixing tank based on the weight of sterile distilled water, and they were heated at a temperature of 80° C. for 1 hour and mixed. Then, whether the gelatin had been solized or not was checked, and 7% by weight of a kaolin solution was added to the solized mixed solution and mixed, followed by stirring the mixed solution to a constant speed of 450 rpm for 30 minutes. After the stirred mixed solution was injected into a cooler and stirred to 150 rpm at a temperature of 4° C. to impart a viscosity of 3,000 cps to the mixed solution, and bubbles were removed from the mixed solution to which the viscosity of 3,000 cps had been imparted at room temperature of 25° C., the bubble-removed mixed solution was infused into a syringe.

Experimental Example

Cytotoxicity Test (MTT Assay)
Effects on cell lysis, cell growth inhibition, colony formation, and other cells due to medical devices and raw materials or eluates thereof can be measured using cell culture techniques.
Tetrazolium assay using an MTT reagent uses the principle that yellow water-soluble MTT tetrazolium is reduced to blue violet water-insoluble MTT formazan crystals as the ring structure of tetrazolium is cut by dehydrogenase in the mitochondria of living cells where metabolic processes are intact by treating yellow water-soluble MTT tetrazolium on the cells.
MTT formazan crystals are generally dissolved in an organic solvent such as dimethyl sulfoxide (DMSO) to measure absorbance using an ELISA reader.
After seeding human primary cells in a 96-well cell plate, they were attached to the cell plate for 24 hours, and then treated with the MTT Cell Proliferation Assay Kit every 24 hours and 48 hours, followed by checking with a wavelength of 490 nm.
Blood Clotting Test
A test was performed to confirm the phenomenon that the clotting factor cascade is activated and occurred.
12-week-old SD male rats were prepared and anesthetized using Avertin anesthetic.
After obtaining blood through the Cardiac blood collection experimental method after anesthesia, the collected blood was put into a tube containing an absorbable haemostatic product for the body, and the time until the blood clotted was measured to check result values.
Haemostatic Performance Test
12-week-old SD male rats were prepared and anesthetized using Avertin anesthetic.
Then, after fixing an experimental animal and cutting the femoral artery, hemostasis was observed while applying and pressing a haemostatic agent to the bleeding site.
After hemostasis was completed, the surgical site was observed at regular intervals to check rebleeding.
[Experiment Results]
Referring to FIG. 2, as results of the cytotoxicity test, it was observed that there were no large differences between the cell viability rates of the haemostatic compositions according to Examples 1 to 5 and the haemostatic compositions according to Comparative Examples 1 to 3, but the haemostatic compositions according to Examples 1 to 5 were slightly high in the cell viability rates compared to the haemostatic compositions according to Comparative Examples 1 to 3. It can be seen from this that when gelatin or/and kaolin is/are mixed, cell proliferation becomes active.
Referring to FIG. 3, the blood clotting rates were shown to be high in Examples 3 to 5 and Comparative Examples 2 and 3, and it could be seen from this that the blood clotting rates became higher depending on the content of kaolin. However, in the case of Example 4, it could be confirmed that the blood clotting rate was not increased simply depending on the content of kaolin by seeing the fact that the blood clotting rate was higher than that of Example 5 having a large content of kaolin.

That is, referring to FIGS. 4 and 5, it can be seen that the blood clotting rate is higher when the kaolin content is 4% than when the kaolin content is 5%, and because of this, it could be confirmed that the blood clotting rate is not increased simply when the kaolin content is high, and it could be seen that the mixed content of kaolin and gelatin is important.

TABLE 1

|  | Hemostasis time (1st) | Hemostasis time (2nd) | Hemostasis time (3rd) |
| --- | --- | --- | --- |
| Example 1 | 9 minutes | 10 minutes | 8 minutes |
| Example 2 | 8 minutes | 9 minutes | 7 minutes |
| Example 3 | 5 minutes | 4 minutes | 5 minutes |
| Example 4 | 1 minute 30 seconds | 2 minutes | 1 minute 40 seconds |
| Example 5 | 5 minutes | 6 minutes | 6 minutes |
| Comparative Example 1 | N/A | N/A | N/A |
| Comparative Example 2 | N/A | N/A | N/A |
| Comparative Example 3 | N/A | N/A | N/A |

Referring to [Table 1], it can be observed that the hemostasis of Example 4 is rapidly performed compared to that of Examples 1 to 3 and 5, and it can be seen that the hemostasis time of Example 3 is short compared to that of Example 5 having a high kaolin content. It can be seen from this that, although the content of kaolin is also important, the content ratio with gelatin is important.

Meanwhile, referring to FIG. 6, the haemostatic composition according to the present disclosure and a commercially available haemostatic product are explained by comparison. When performing hemostasis through the haemostatic composition according to the present disclosure and commercially available haemostatic product after inducing hemostasis, it can be seen that, although hemostasis occurs after 2 minutes in the case of the haemostatic composition according to the present disclosure, rebleeding appears after 5 minutes in the case of the haemostatic product. Therefore, it can be confirmed that haemostatic effects such as enabling rapid hemostasis, enabling the hemostasis time to be shortened, and others can be achieved by enabling the hemostasis speed of the bleeding site to be accelerated compared to existing haemostatic products when using the haemostatic composition in a state that the haemostatic composition according to the present disclosure is contained in the haemostatic products.

Hereinabove, the present disclosure has been shown and described in relation to specific embodiments, but those of ordinary skill in the art will be easily able to see that various modifications and changes are possible within the limits that do not depart from the spirit and scope of the present disclosure as set forth in the appended claims.

What is claimed is:

1. A method for preparing an injectable absorbable haemostatic composition for the body, the method comprising:
   (i) mixing gelatin with sterile distilled water;
      wherein the gelatin is mixed in an amount of 5 to 7 parts by weight with respect to 100 parts by weight of the sterile distilled water;
   (ii) solizing the mixture from step (i);
      wherein the solization is performed by stirring the mixture at 300 rpm in a temperature range of 70 to 80° C. for 1 hour;
   (iii) mixing kaolin with the solized mixture from step (ii);
      wherein the kaolin is mixed in an amount of 4 parts by weight with respect to 100 parts by weight of the sterile distilled water, and then the solized mixture with which kaolin has been mixed is stirred at 350 to 450 rpm in a temperature range of 70 to 80° C. for 30 to 40 minutes;
   (iv) imparting viscosity to the mixed gelatin kaolin solution from step (iii);
      wherein imparting viscosity to the mixed gelatin kaolin solution comprises injecting the mixed gelatin kaolin solution into a cooler, stirring the mixed gelatin kaolin solution at 100 to 500 rpm in a temperature range of 4 to 5° C. on a cooling plate provided on the bottom surface of the cooler, thereby imparting a viscosity of 3,000 cps;
   (v) removing bubbles from the mixed gelatin kaolin solution having a viscosity of 3,000 cps at room temperature of 25° C.; and
   (vi) infusing the bubble-removed mixed solution from step (v) into a syringe.

* * * * *